United States Patent [19]
Flower

[11] Patent Number: 5,876,368
[45] Date of Patent: Mar. 2, 1999

[54] IONTOPHORETIC DRUG DELIVERY DEVICE HAVING IMPROVED CONTROLLER

[75] Inventor: Ronald J. Flower, Vernon, N.J.

[73] Assignee: Becton Dickinson and Company, Franklin Lakes, N.J.

[21] Appl. No.: 706,926

[22] Filed: Sep. 3, 1996

Related U.S. Application Data

[62] Division of Ser. No. 315,377, Sep. 30, 1994, abandoned.

[51] Int. Cl.$^6$ ...................................................... A61N 1/30
[52] U.S. Cl. ............................................. 604/20; 604/49
[58] Field of Search ................................... 604/20–21, 49

[56] References Cited

U.S. PATENT DOCUMENTS

| | | |
|---|---|---|
| 4,819,657 | 4/1989 | Kraft et al. . |
| 5,167,617 | 12/1992 | Sibalis . |
| 5,169,384 | 12/1992 | Bosniak et al. . |
| 5,234,404 | 8/1993 | Tuttle et al. . |
| 5,551,953 | 9/1996 | Lattin et al. . |
| 5,571,149 | 11/1996 | Liss et al. . |
| 5,697,896 | 12/1997 | McNichols et al. . |

FOREIGN PATENT DOCUMENTS

| | | |
|---|---|---|
| 454917 | 12/1974 | U.S.S.R. . |
| 2 239 803 | 7/1991 | United Kingdom . |
| WO 86/07269 | 12/1986 | WIPO . |
| WO 92/10234 | 6/1992 | WIPO . |
| WO 93/03790 | 3/1993 | WIPO . |

*Primary Examiner*—Mark Bockelman
*Attorney, Agent, or Firm*—Hoffmann & Baron, LLP

[57] ABSTRACT

An iontophoretic drug delivery device including an improved controller is disclosed. More specifically, the controller includes a number of features including a controller which records the number of times that it has been used. The controller records the number of uses and, after a predetermined number of uses, the controller will no longer operate. Similarly, the controller may include a microprocessor which times a useful life of the controller, such as five (5) years. Once the timer has timed a predetermined length of time, the controller will indicate that it is no longer useable and should be discarded. The microprocessor of the controller may also be used for storage of a unique serial number embedded in the read only memory of the microprocessor for traceability purposes. Additionally, the unique serial number may be used as a security measure to ensure that the correct controller is used with the proper patch. The microprocessor of the controller may also be used to record a date, time and/or duration of usage and playback the recorded information to a health-care professional. One method of transmitting and receiving the information from the controller is to use an LED indicator. The LED can be used as a photoreceiver as well as a transmitter of information.

10 Claims, 3 Drawing Sheets

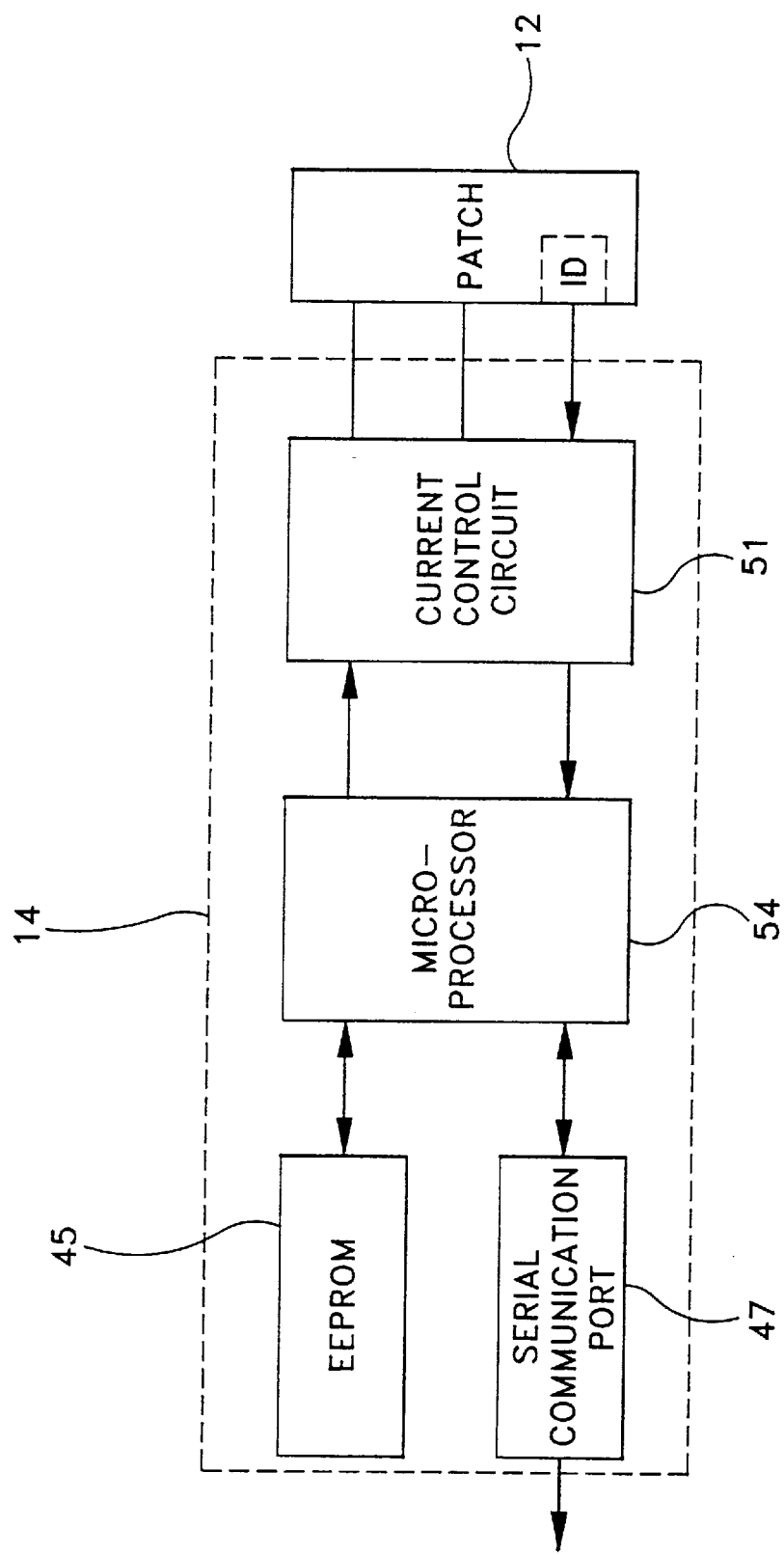

IONTOPHORETIC DRUG DELIVERY DEVICE HAVING IMPROVED CONTROLLER

This is a divisional of application, U.S. Ser. No. 08/315,377 filed on Sep. 30, 1994 now abandoned.

BACKGROUND OF THE INVENTION

1. Field of the Invention

The present invention relates to an improved controller for an iontophoretic drug delivery device, and more particularly relates to a controller having a number of features which improve usability and traceability of the iontophoretic drug delivery device.

2. Background of the Related Art

Iontophoresis may be defined as the introduction of medicaments by means of an electric current into the tissues of the body for therapeutic purposes. Iontophoretic devices, have, in recent years, become an increasingly important means of administering therapeutic agents. Such systems offer advantages clearly not achievable by any other methods of administration, such as by ingestion or by injection through the skin.

Presently, known iontophoretic devices use at least two electrodes, which are in contact with a portion of a patient's body. A first electrode, generally called the active electrode, delivers the ionic substance or drug into the body by iontophoresis. The second electrode, generally called the counter electrode, closes an electrical circuit that includes the first electrode and the patient's body. Generally, the circuit includes a source of electrical energy, such as a battery. The ionic substance to be driven into the body may be either positively charged or negatively charged. In the case of a positively charged ionic substance, the anode of the iontophoretic device becomes the active electrode and the cathode serves as the counter electrode to complete the circuit. Alternatively, if the ionic substance to be iontophoreticly delivered is negatively charged, the cathode will be the active electrode and the anode will be the counter electrode.

One type of iontophoretic drug delivery device includes a separate, reusable controller, which can be removably, electrically coupled to a patch containing the therapeutic agent. The controller includes the electronics which control the amount of current applied to the patch as well as the duration of the applied current. Delivery of a drug to the patient may be accomplished at a constant rate over a long period of time or, alternatively, at periodic intervals. Thus, it may be necessary for the drug-containing patch to be maintained in contact with the patient's skin for a long period of time, either for continuous drug delivery, or to permit frequent interval delivery over a period of time.

In situations where the periodic delivery of the medicament is indicated, there is no need to maintain the source of electric current connected to the patch between doses. While the unobtrusive medicament-containing patch may remain attached to the patient, removability of the current source would permit the patient to be free from cumbersome connection to the current source between doses. At such time as iontophoretic drug delivery is once again necessary, the medicament-containing patch attached to the patient's skin may be reconnected to the current source. Since the current source generally includes a battery, it would be helpful to know the number of times the controller has been used as well as the duration of the use. In this manner, one can ensure that the controller has sufficient energy to transdermally deliver the necessary dosage of medicament to the patient.

In situations where the iontophoretic device is applied by the patient himself, it would be helpful to health-care professionals to be able to determine if the patient has actually received the medication. For example, it would be beneficial if the controller could communicate with the health-care professional to provide proof that it has actually delivered the medication to the patient.

As previously noted, it may be necessary to use an iontophoretic drug delivery device over an extended period of time i.e., longer than 24 hours to delivery the necessary dosage of drug. As the length of delivery time increases, there is a need to develop small, unobtrusive iontophoretic delivery devices which can be easily worn on the skin under clothing.

In addition to the need for developing smaller iontophoretic devices, there is need to reduce the cost of these devices in order to make them more competitive with conventional forms of therapy such as pills and subcutaneous injections. One manner of improving cost effectiveness is to have a reusable controller which includes the costly electronics that provides the current to drive the patch.

It is an object of the present invention to provide an improved iontophoretic drug delivery device having a reusable controller which can record the number of times the controller has been used.

It is a further object of the present invention to provide an improved iontophoretic drug delivery device having a controller which includes a clock for timing a useful life of the controller.

It is still a further object of the present invention to provide an iontophoretic drug delivery device having a unique serial number embedded in the controller electronics for purposes of traceability and security.

It is yet a further object of the present invention to provide an iontophoretic drug delivery device having a controller which is capable of recording dates, times and/or duration of usage and provide the resulting information to a health-care professional to evaluate patient compliance in receiving prescribed medication.

It is yet a further object of the present invention to provide an improved iontophoretic drug delivery device having a controller which includes an LED indicator. The LED indicator is capable of sending information from the controller to a health-care professional. Additionally, the LED can act as a photo receiver to receive information to thereby instruct the controller.

SUMMARY OF INVENTION

In accordance with one embodiment of the present invention, the iontophoretic drug delivery device includes a medicament-containing disposable patch and a reusable controller selectively connectable to the patch. The patch is removably attachable to the skin of the patient for transdermal delivery of ionized medicament. The controller provides an energy source that powers the patch to drive the ionized medicament transcutaneously to the patient. The controller further includes a means for sensing a number of times the controller is used. In this manner, the useful life of the iontophoretic controller can be tracked. In order to accomplish this task, the iontophoretic drug delivery device includes a microprocessor which counts the number of times the controller has been applied. Additionally, the microprocessor renders the controller unusable when a specific number of applications have been sensed to ensure that sufficient energy remains in the power source to drive the ionized medicament transcutaneously to the patient. The controller may further include a display for displaying the number of times the controller has been used and for indicating whether a useful life of the controller has expired.

In an alternative embodiment, the iontophoretic drug delivery device includes a clock, which can be started at the date of manufacture, for timing a useful life of the controller. For example, the power source may have a life of approximately 5 years. Accordingly, when the clock has timed 5 years from the date of manufacture, the controller is no longer usable and should be discarded. The controller may include indication means to indicate that the useful life has expired and, additionally, includes a means to render the controller unusable when the predetermined time period has expired.

The iontophoretic drug delivery device in accordance with the present invention also includes a means for recording a date, time and/or duration of usage by the patient. This stored information can be transmitted to a health-care professional to evaluate patient compliance in receiving medication as prescribed. The recordation means includes a microprocessor to record the information and a means for transmitting the stored information from the microprocessor to the health-care professional. The transmitting means may take any known form such as a serial port of the microprocessor or an LED which can act as a transmitter and photo receiver for receiving instructions from the microprocessor. The controller in accordance with the present invention having the recording feature, provides a fail-safe drug delivery system, so that the health-care professional can determine if the patient is actually receiving the medication prescribed. For example, the controller can inform the health-care professional that either it never delivered current to the patch or can provide proof that medication was delivered at a particular time, and on a particular date, so that the health-care professional can be assured that the patient received the medication as prescribed.

The iontophoretic device in accordance with the present invention may also include a unique serial number stored in the read only memory (ROM) of the microprocessor. The purpose of the unique serial number is for traceability or tracking of the controllers. Accordingly, the controller can be tracked to determine which patient has a particular controller. Additionally, a physician or health-care professional may check the serial number to determine if a wrong patient is using the controller. Furthermore, the unique controller serial number may be used as a security device. More particularly, the patch may also include a unique serial number which can be read by the controller. A microprocessor within the controller can compare the serial number of the patch with the serial number of the controller to ensure compatibility of the controller to the patch. It is important when using reusable controllers to ensure that the proper amount of current for the proper amount of time is applied to the patch to drive the specific medicament within the patch transcutaneously to the patient.

A preferred embodiment of the iontophoretic drug delivery device, as well as other embodiments, objects, features and advantages of this invention, will be apparent from the following detailed description, which is illustrated in the accompanying drawings.

BRIEF DESCRIPTION OF THE DRAWINGS

FIG. 5 is a block diagram of an iontophoretic device having a microprocessor in accordance with the present invention.

DETAILED DESCRIPTION OF THE PREFERRED EMBODIMENT

Figure 1:
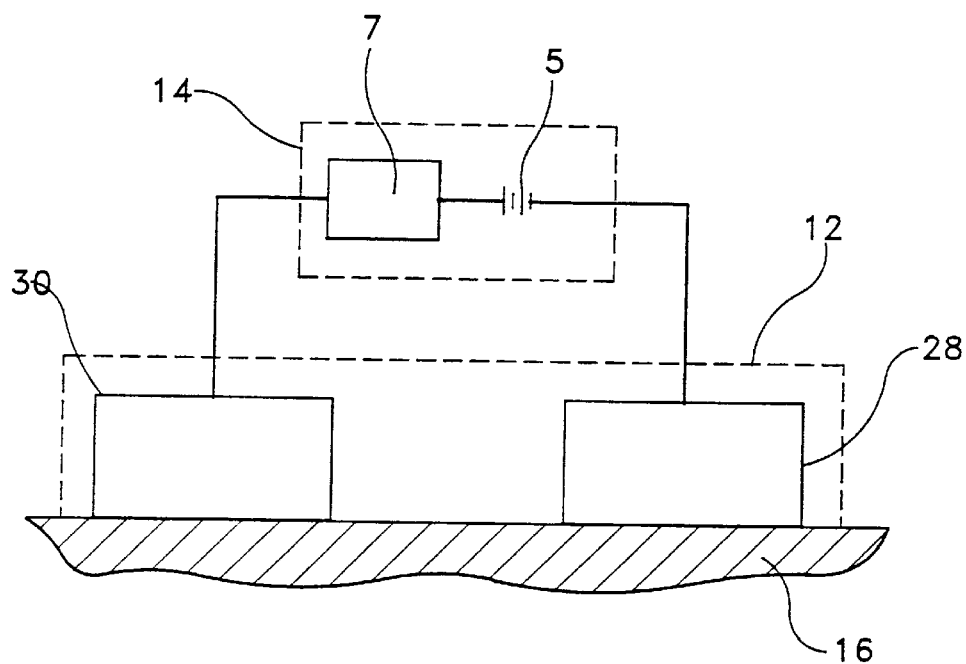
FIG. 1 is a schematic illustration of an iontophoretic drug delivery device formed in accordance with the present invention.

Referring to FIG. 1, an iontophoretic drug delivery device in accordance with the present invention includes a patch 12 attached to the skin of a patient 16 and a controller 14 electrically connected to the patch 12. The patch includes an active electrode assembly 28 and a counter electrode assembly 30. If a positively charged medicament is to be delivered to the skin 16, the medicament would be positioned in the active electrode assembly. As shown in FIG. 1, the iontophoretic drug delivery device also includes a controller 20 having a power supply 5 and a control circuit 7. The controller 14 is coupled to the patch 12 using well known means, for example, by printed flexible circuits, metal foils, wires, tabs or electrically conductive adhesives. The power supply 5 in combination with the electrode assemblies 28 and 30 and the patient's body 16 completes the circuit and generates an electric field across the body surface or skin to which the iontophoretic device is applied. The electric field generated by the power supply 5 causes the medicament in the electrode assembly 28 to be delivered into the body of the patient by the process of iontophoresis.

Figure 2:
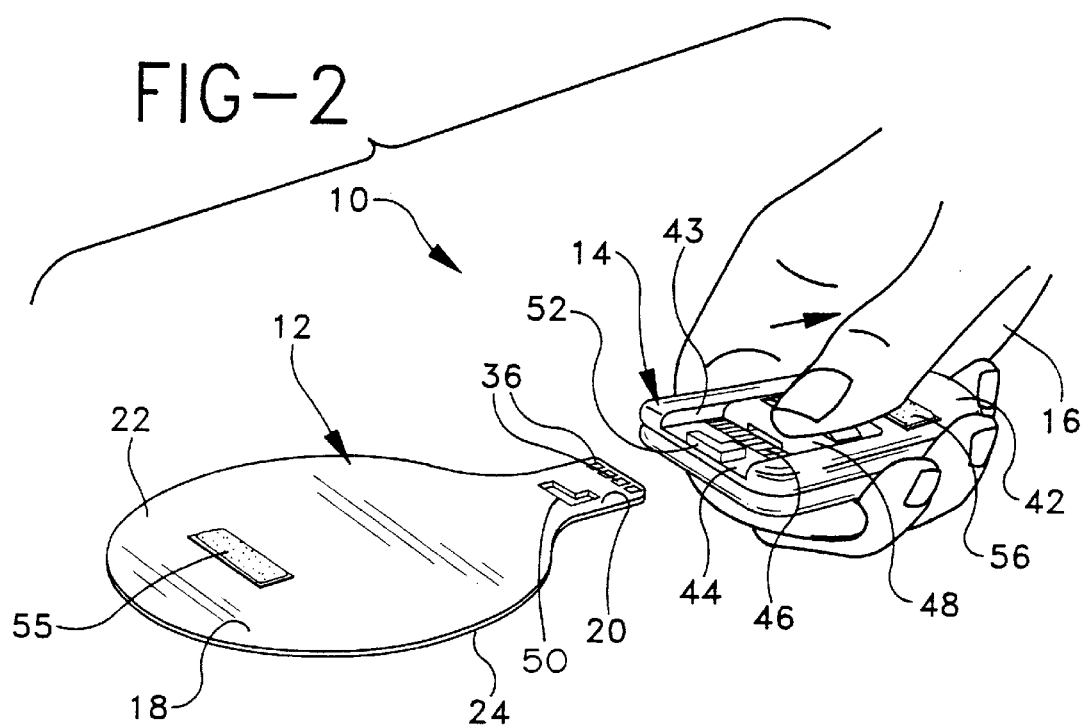
FIG. 2 is a perspective view of an iontophoretic patch and a reusable controller of the present invention shown prior to connection.
Figure 3:
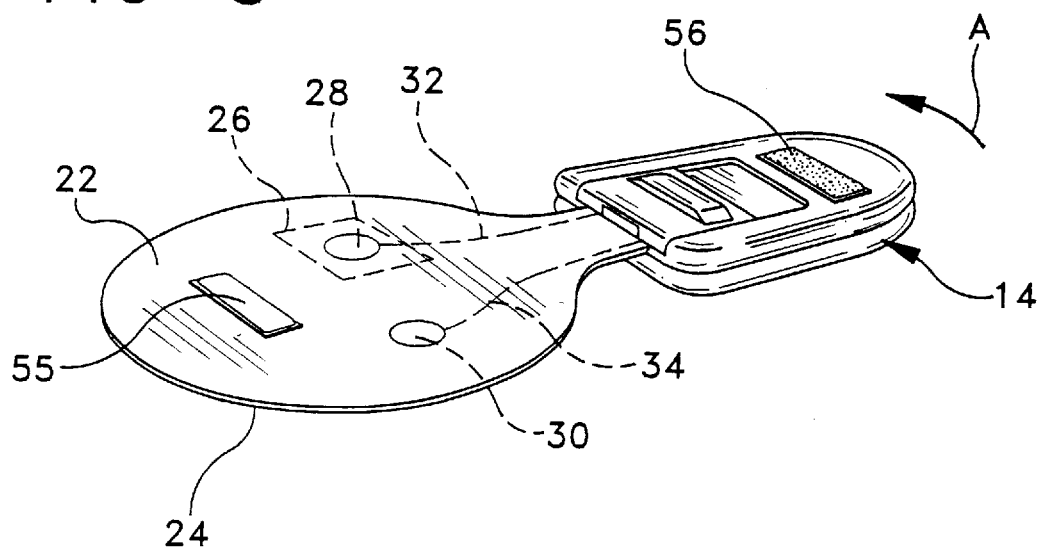
FIG. 3 is a perspective view of an iontophoretic patch and controller of the present invention shown after connection.
Figure 4:
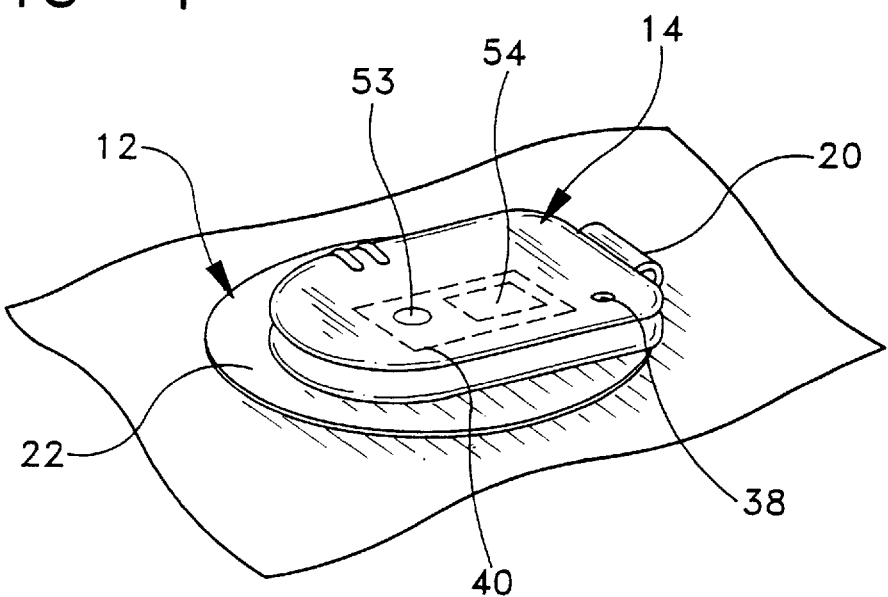
FIG. 4 is a perspective illustrating the iontophoretic drug delivery device of the present invention attached to the skin of the patient.

Referring to FIGS. 2 and 3, an iontophoretic drug delivery device 10 including patch 12 and controller assembly 14 of the present invention is shown. Patch 12 is a generally planar flexible member formed of biocompatible material. Patch 12 may be formed of woven or non-woven textiles or polymers or may be any other construction well known in the art. Patch 12 is adhesively supported on the skin 16 of the patient (FIG. 4). Patch 12 includes an enlarged patch body 18 and an extending narrow tab 20. Patch body 18 includes opposed planar surfaces 22 and 24. Planar surface 24 is disposed for skin contact and includes a drug (i.e., medicament) reservoir 26 (shown in phantom in FIG. 3) which contains an ionic drug typically in a gel form. While reservoir 26 is shown, any other known iontophoretic drug reservoir structure for placing a medicament in contact with the skin in an iontophoretic patch may be employed.

Skin contacting surface 24 further includes a pair of spaced apart electrodes 28 and 30. Each of electrodes 28 and 30 are positioned to be in contact with the skin once the patch 12 is secured, as shown in FIG. 4. The positioning of electrodes 28 and 30 is such that an electrical current path is established between electrodes 28 and 30 through the skin of the patient. Electrode 28 is also placed in conductive contact with reservoir 26 in a manner well-known in the iontophoretic delivery art. A direct current source may be connected between the electrodes 28 and 30 such that electrode 28 in contact with reservoir 26 assumes the same charge as the ionized drug contained in reservoir 26. Under the influence of electrical current passing from the electrode 28 to electrode 30 through the skin, the drug contained in reservoir 26 is transcutaneously delivered.

Referring to FIG. 3, electrical current is supplied from the controller 14 to electrodes 28 and 30 on the patch via electrical traces 32 and 34. Each of traces 32 and 34 may be one or more conductive paths extending from electrodes 28 and 30 to exposed conductive pads 36 (FIG. 2) positioned on a marginal edge of the patch tab 20. As described in further detail below, pads 36 are positioned for electrical connection to the controller 14, which provides a source of electrical current.

Referring back to FIG. 3, controller 14 houses electronic components 40 that control the supply of electric current to electrodes 28 and 30. As is known in the art, electrical components 40 may include a source of electrical power such as a battery 42 and additional electronic components, such as a microprocessor 44, used to send a controlled electrical current to electrodes 28 and 30.

As illustrated in FIGS. 2 and 3, controller 14 includes a controller housing 42 which is generally rectangular in shape and includes an open front end 44 which accommodates tab 20 of patch 12. Housing 42 further accommodates a connection array 46 adjacent electronic components 40 (FIG. 4). The connection array 46 and electronic components are preferably mounted to a common printed circuit board (not shown). Connection array 46 may include plural electrical terminals in electrical connection with electronic components 40 and which are connectable to pads 36 of tab 20. In the present illustrative embodiment, connection array 46 is an electrical connection device having plural spaced-apart, exposed conductive surfaces separated by an insulating material. It may be appreciated that any suitable electrical interconnection device may be employed in accordance with the present invention.

Housing 42 further includes a cover 48 which is used to close the open front end 44 of housing 42. Cover 48 is slidably, captively retained on an upper wall 43 of housing 42. As shown in FIG. 2, cover 48 may be manually moved under thumb actuation to an open position exposing connection array 46 for electrical connection with pads 36 of tab 20. Cover 48 may be moved to a closed position shown in FIG. 3, covering connection array 46. With cover 48 in an open position patch 12 may be connected to controller 14.

In order to assure accurate alignment of pads 36 of tab 20 with the connection array 46 supported within housing 42, tab 20 is keyed to housing 42. Tab 20 includes an opening 50 which is designed to fit over an upwardly extending post 52. Opening 50 and post 52 are of similar shape so as to provide keyed accommodation of tab 20 and post 52. Post 52 extends upwardly from a bottom wall 45 of housing 42 adjacent the open front end 44. Post 52 is centrally located adjacent connection array 46 to accommodate tab 20 and positionally confine tab 20 within housing 44. The key structure included on both opening 50 and post 52 prevents incorrect positioning of patch 12 with respect to controller 14. In the present embodiment, both opening 50 and post 52 have a generally L-shaped cross-section, however, any other mating shape which would prevent incorrect alignment may be employed.

Referring again to FIG. 3, patch 12 and controller 14 includes attachment means for permitting the releasable support of controller 14 on patch 12 after interconnection between pads 36 and connective array 46 is established. Surface 22, which is opposed to skin-engaging surface 24 of patch 12, and the upper surface of housing wall 43 include cooperating fastening elements 55 and 56 thereon. In the present illustrative embodiment, the cooperative fastening elements include conventional hook and loop fasteners of the type sold under the trademark VELCRO. Any other cooperating type fasteners may be employed to achieve the same objective. One cooperating fastening element 55 is secured adhesively or otherwise to patch 12 on surface 22 while the other cooperating fastening member 56 is secured by adhesive or otherwise to the upper surface of wall 43 of housing 42. As described in further detail below, attachment of the mating hook and loop fasteners 55 or 56 provide removable support for controller 14 on patch 12. It may be appreciated by those skilled in the art that the patch and controller may take any known form. The only requirement is that the patch be capable of being physically and electrically connected to the controller.

Having described one embodiment of iontophoretic drug delivery device 10 of the present invention, its operation is described below.

Patch 12 may be adhesively secured to the skin 16 of the patient. Surface 24 of patch 12 is placed in intimate contact with the skin 16 so that electrodes 28 and 30, as well as drug containing reservoir 26, are supported in intimate contact with the skin 16. In order to iontophoretically deliver the medicament from reservoir 26 transcutaneously through the skin 16, reusable controller 14 is electrically connected to patch 12. Housing 42 is slipped over extending tab 20 of patch 12 so that opening 50 in tab 20 is seated over upwardly extending post 52 of housing 42. Proper planar orientation is assured between patch 12 and controller 14 due to the key matability between opening 50 and post 52. As controller 14 is designed to be maintained in electrical connection with patch 12 during iontophoretic delivery of the drug contained in reservoir 16, controller 14 may be fastened to patch 12 so that it will be conveniently retained on the skin of the patient.

As shown in FIG. 3, once patch 12 is connected to controller 14, the controller may be flipped up in the direction of arrow A so that the mating hook and loop fasteners 55 and 56 engage each other to removably fasten controller 14 to patch 12 as shown in FIG. 4. The controller 14 is comfortably retained on the skin of the patient during iontophoretic drug delivery. At such time as a particular application of the drug is completed, the controller may be removed by separating the mating hook and loop fasteners 55 and 56. The controller may be disconnected and placed aside until the next administration of the drug is needed. The patch 12 may remain on the skin of the patient, eliminating the need for frequent replacement of the patch.

As previously indicated, when using a reusable controller, it would be advantageous to have a means for counting the number to times the controller has been used. Since the controller includes the electronics and more particularly, the power source, the controller can only be used a specific number of times before the battery power is depleted. For example, a controller which is specifically programmed to provide current to a patch administering a specific medicament may need to operate at a certain current level for two hours in order to deliver the proper dosage. Under the conditions, the life expectancy of the controller may hypothetically be calculated to be 200 applications. In this situation, the controller preferably includes means for counting the number of applications and, when the maximum number has been counted, the controller includes a means for indicating it is no longer usable.

In the preferred embodiment of the present invention, the reusable controller includes electronics 40 (FIG. 4) that control the current applied to a patch. The controller electronics includes a battery 42 and a microprocessor 44. Other suitable electronics may be mounted on a printed circuit board incorporated within the controller housing. Among its other functions, the microprocessor 44 detects each time the controller is used and maintains a running total. Once, the microprocessor counts a specific number of applications, e.g. 200, the microprocessor disables the controller from further applications. In this way, it can be assured that the controller has sufficient energy to drive the medicament from the patch to the patient's body so that the patient will receive a proper dosage. The controller preferably includes a means to indicate that the useful life of the controller has been exhausted. For example, referring to FIG. 4, the controller may include a visual (or audible) indicator, such as an LED or LCD 43, which will be illuminated or turned off when the controller is no longer usable.

In an alternate embodiment, the useful life of the reusable controller may be stored by a clock in the controller microprocessor. For example, the controller power source may have a calculated life expectancy, based upon the preprogrammed power requirements and shelf life of the battery, to drive a series of patches for approximately five years. The clock may be started at the time of manufacture of the controller. When the microprocessor has determined that the preprogrammed amount of continuous time from manufacture has expired, the controller will be rendered unusable and may be discarded or returned to the manufacturer. The controller may include similar indication means, such as an LED, to visually indicate to the user that the controller can no longer be used. Such a technique would be analogous to the expiration date on a bottle of pills. The manufacturer can thus be assured that an out-of-date controller can be rendered unusable, and this safety technique may satisfy some of the product liability concerns of the manufacturer.

The indicator 43 may be coupled to a driver circuit (not shown) which is responsive to a signal provided by the microprocessor 44. The microprocessor 44 will compare the running total of uses of the controller with a predetermined value, and if the running total equals the predetermined value, or has approached within a preselected number of times of the predetermined value, for example, a signal to the indicator driver circuit will cause the driver circuit to turn on or turn off the indicator. In this way, the patient will know that the controller can no longer be used and a new controller must be purchased.

When using an iontophoretic drug delivery device, having a reusable controller, it would also be advantageous to identify which patient has a particular controller. Such a tracking system may include a unique serial number embedded in the controller. Referring to FIG. 5, the unique serial number or prescription can be embedded in the read only memory (ROM) of the microprocessor. One method would be to permanently store the unique serial number in E$^2$PROM at the time of manufacture, or at the physician's office or pharmacy. The unique serial number can be read through a serial port by a health-care professional to determine the identification of the controller for tracking upon distribution. In FIG. 5, the controller 14 is electrically connected to the patch 12. The controller includes a current control circuit 51 and a microprocessor 44 includes an E$^2$PROM 45 and a serial communication port 47. The traceability of the reusable controllers is significantly enhanced by the readable unique serial number. Accordingly, a doctor or outside agency will be able to check the serial number to ensure that the correct patient has received the correct controller.

Additionally, the unique controller serial number may be used as a security device to ensure that the proper patch has been connected to the proper controller. An identification of the patch may be read into the microprocessor of the controller and compared to the unique controller serial number. If the microprocessor determines that the patch and controller, based upon its identification, are incompatible, the microprocessor will not allow current to be applied to the patch.

As well as traceability of the controllers, it would be advantageous to health-care professionals to have the ability to determine if the patient is receiving the desired dosage of medication. The controller of the present invention advantageously includes a microprocessor having an E$^2$PROM having a sufficient memory to be able to record the date, time and/or duration of usage. The stored information may be played back by a technician or health-care professional. This becomes extremely important in monitoring a patient who is iontophoretically administering the drug away from a clinical setting. Using known electronics and microprocessor, such as microchip PIC 16C71-04/50, manufactured by Microchip Technology, Inc. of Chandler, Ariz., the controller voltage, current, and duration of use can be recorded and stored for subsequent playback. Referring to FIG. 5, the stored information may be played back through the serial communications port of the controller. The recorded information can provide the necessary information to ensure that a proper dosage of medicament has been administered to the patient.

In an alternative embodiment, the controller includes an LED 43 (FIG. 4) which can send and receive information to instruct the microprocessor. The LED is electrically coupled to the microprocessor so that information received and stored by the microprocessor can be transmitted via the LED to a technician or health-care professional. The stored data may be transmitted by the LED to a computer and displayed using any known means such as the display of the computer. Additionally, during the off time of the LED, the LED can be used as a photo-receiver for providing instructions or programming to the microprocessor in the controller. Accordingly, the improved iontophoretic drug delivery controller allows for two-way communication to receive data accumulated by the controller during use and to provide altered or new instructions to the controller without disassembly. The circuitry for performing the transmitting and receiving using LED's is well known to those skilled in the art and any such known circuitry may be used to accomplish this feature.

The present invention offers many features that are needed in the administration of medicaments by the use of iontophoretic devices. The improved controller of the present invention is capable of recording important information and playing the information back to healthcare professionals. Additionally, the controller and patch design include important safety features to ensure the patient's safety misapplication of medicaments or excessive current to the patient.

Although illustrative embodiments of the present invention have been described, it is to be understood that the invention is not limited to those precise embodiments, and that various other changes and modifications may be effected therein by one skilled in the art without departing from the scope or spirit of the invention.

I claim:

1. An iontophoretic drug delivery device comprising:
   a medicament-containing disposable patch removably attachable to the skin of a patient for transdermal delivery of ionized medicament; and
   a reusable controller removably, electrically connectable to said patch, the controller providing sufficient energy to said patch to drive the ionized medicament into the skin of a patient, the controller further including a microprocessor for recording a date and time of usage for evaluating patient compliance in receiving medication as prescribed and output means for playing back the recorded information in said microprocessor, wherein the output means comprises an LED.

2. An iontophoretic drug delivery device as defined in claim 1, wherein said LED transmits information stored in the microprocessor to a means for displaying said information.

3. An iontophoretic drug delivery device as defined in claim 2, further including input means wherein the LED further acts as a photo-receiver for receiving information from an external source for programming said microprocessor in the controller.

4. A method to determine if a patient is receiving medication via an iontophoretic device, comprising a medicament-containing disposable patch removably attachable to the skin of a patient for transdermal delivery of medication and a controller electrically connectable to the patch, the controller providing sufficient energy to drive the ionized medicament into the skin of the patient, the controller further including means for recording information, the method comprising the steps of:

recording a date, time and duration of usage of the iontophoretic drug delivery device; and playing back the recorded information via an LED connected to said controller to transmit the recorded information to a display to determine if the patient has received a proper dosage of medication.

5. An iontophoretic drug delivery device comprising:

a medicament-containing disposable patch removably attachable to the skin of the patient for transdermal delivery of ionized medicament; and a reusable controller removably, electrically connectable to said patch, the controller providing sufficient energy to said patch to drive the ionized medicament into the skin of a patient, said controller further including a microprocessor and an LED electrically connected to said microprocessor, said LED capable of being a transmitter for transmitting information obtained and stored in said microprocessor and a photo receiver for receiving information to instruct said microprocessor.

6. The iontophoretic drug delivery device of claim 5, wherein said information obtained and stored in said microprocessor is selected from the group consisting of controller voltage, controller current, duration of use, and combinations thereof.

7. The iontophoretic drug delivery device of claim 5, wherein said information obtained and stored in said microprocessor is selected from the group consisting of date of use, time of use, duration of use, and combinations thereof.

8. The iontophoretic drug delivery device of claim 5, wherein said information received by the photo receiver comprises programming instructions to said microprocessor.

9. The iontophoretic drug delivery device of claim 5, wherein said information obtained and stored in said microprocessor comprises a count of the number of applications administered from said patch.

10. The iontophoretic drug delivery device of claim 5, wherein said information obtained and stored in said microprocessor comprises a unique serial number associated with said controller.

* * * * *